United States Patent
Chodorow et al.

(10) Patent No.: US 7,370,658 B2
(45) Date of Patent: May 13, 2008

(54) DENTAL FLOSSER WITH BENDABLE HEAD

(75) Inventors: Ingram S. Chodorow, San Diego, CA (US); Scott D. Salmon, Tenafly, NJ (US)

(73) Assignee: Placontrol, Inc., San Diego, CA (US)

( * ) Notice: Subject to any disclaimer, the term of this patent is extended or adjusted under 35 U.S.C. 154(b) by 358 days.

(21) Appl. No.: 10/942,616

(22) Filed: Sep. 15, 2004

(65) Prior Publication Data

US 2005/0217692 A1 Oct. 6, 2005

Related U.S. Application Data

(60) Provisional application No. 60/503,618, filed on Sep. 15, 2003, provisional application No. 60/542,534, filed on Feb. 6, 2004.

(51) Int. Cl.
*A61C 15/00* (2006.01)

(52) U.S. Cl. ............... 132/323; 132/324; 132/325; 132/326; 132/327

(58) Field of Classification Search ........ 132/322, 132/323–327
See application file for complete search history.

(56) References Cited

U.S. PATENT DOCUMENTS

| 844,181 | A | * | 2/1907 | Overbaugh | 132/324 |
|---|---|---|---|---|---|
| 1,306,998 | A | * | 6/1919 | Dimitroff | 132/325 |
| 1,417,518 | A | * | 5/1922 | Henerlau | 132/324 |
| 1,882,204 | A | * | 10/1932 | Zrna | 132/323 |
| 3,236,247 | A | | 2/1966 | Brockman | |
| 3,533,420 | A | * | 10/1970 | Maloney et al. | 132/325 |
| 4,006,750 | A | | 2/1977 | Chodorow | |
| 4,016,892 | A | | 4/1977 | Chodorow | |
| D244,376 | S | | 5/1977 | Chodorow | |
| D250,214 | S | | 11/1978 | Chodorow | |
| 4,192,330 | A | | 3/1980 | Johnson | |
| 4,332,559 | A | | 6/1982 | Dolinsky | |
| D301,071 | S | | 5/1989 | Franchi | |
| 5,067,503 | A | | 11/1991 | Stiles | |
| 5,086,792 | A | | 2/1992 | Chodorow | |
| 5,388,600 | A | | 2/1995 | Hart | |
| 5,538,023 | A | | 7/1996 | Ockowski et al. | |
| 5,692,531 | A | | 12/1997 | Chodorow | |
| 5,829,458 | A | | 11/1998 | Chodorow | |
| D410,115 | S | | 5/1999 | Chodorow | |
| 6,065,479 | A | | 5/2000 | Chodorow | |
| 6,752,158 | B1 | * | 6/2004 | Gwen | 132/327 |

* cited by examiner

*Primary Examiner*—Darwin P Erezo
(74) *Attorney, Agent, or Firm*—Abelman Frayne & Schwab (57) ABSTRACT

A dental flossing device includes: (a) a handle having proximal and distal ends, (b) a flosser head extending from the distal end of the handle, the flosser head having a base, two spaced apart arms extending from the base and having distal ends, and a strand of dental floss extending between and secured to the distal ends of the arms, and (c) a hinge connecting the distal end of the handle to the flosser head, the flosser head having a first position generally co-planar with the handle, the flosser head being bendable about the hinge to a second position that is angled relative to the handle, the arms in the first position of the flosser head being spaced apart a first distance, the device including engagement elements for securing the flosser head in the second position and urging the distal ends of the arms to be spaced apart a second distance greater than the first distance to thus stretch the strand of dental floss to be more taut.

19 Claims, 13 Drawing Sheets

DENTAL FLOSSER WITH BENDABLE HEAD

This application claims benefit of the Sep. 15, 2003 filing date of applicant's prior U.S. Provisional Patent Application No. 60/503,618 and the Feb. 6, 2004 filing date of applicant's prior Provisional Patent Application No. 60/542,534.

BACKGROUND OF THE INVENTION

1. Field of the Invention

This invention is in the field of dental floss holders where a small segment or strand of dental floss is secured between two spaced apart arms which extend from a handle which include dental flossers which are essentially flat, dental flossers having the flosser head bent relative to the handle, and dental flossers having a replaceable flosser head.

| U.S. Pat. No. | Inventor | Date |
| --- | --- | --- |
| 4,006,750 | I. S. Chodorow | Feb. 8, 1977 |
| 4,016,892 | I. S. Chodorow | Feb. 8, 1977 |
| D 244,376 | I. S. Chodorow | May 1977 |
| D 250,214 | I. S. Chodorow | Nov. 7, 1978 |
| D 301,071 | R. Franchi | May 9, 1989 |
| 5,086,792 | I. S. Chodorow | Feb. 11, 1992 |
| 5,538,023 | I. S. Chodorow | Jul. 23, 1996 |
| 5,829,458 | I. S. Chodorow | Nov. 3, 1998 |
| 6,065,479 | I. S. Chodorow | May 23, 2000 |

Figures 5A, 5B:
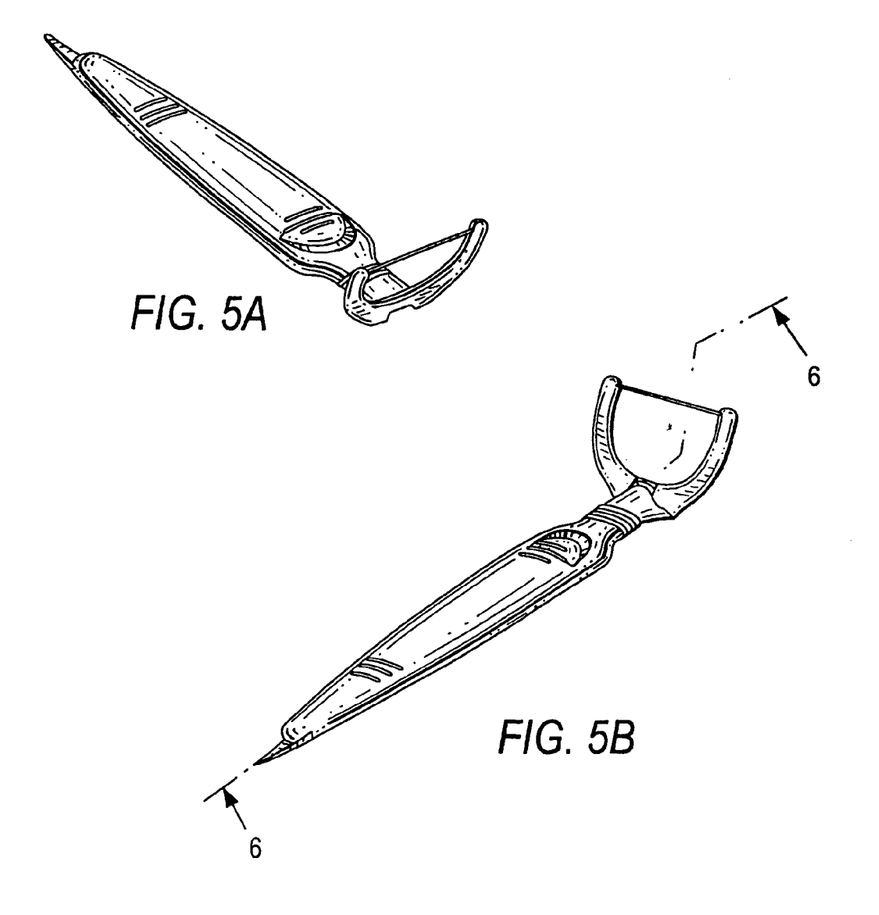
FIG. 5A is a top front perspective view of the new flosser in bent and assembled form.
FIG. 5B is a top rear perspective view of the new flosser in bent and assembled form.

FIG. 5A is a top front perspective view of the new flosser in bent and assembled form.

FIG. 5B is a top rear perspective view of the new flosser in bent and assembled form.

2. Prior Art

Dental flossing devices, also known as dental flossers and dental floss holders, are now popular in the market and are manufactured in both disposable and non-disposable configurations. While some of these dental flossers are relatively large and contain in their handles a spool of floss which is unrolled periodically to provide a new segment of floss spanning the spaced apart fingers, other dental flossers are generally flat for ease of packaging and for ease and convenience of carrying in one's pocket. These flossers are also inexpensive, are promoted as disposable, and have a segment of floss permanently embedded in and spanning a pair of arms.

Prior art flossers have often been made using styrene for the handles and Nylon for the dental floss. In the manufacture of such flossers, the highly stretchable Nylon floss is positioned in the mold and tensioned before injection of the fluid plastic to form the handle. Subsequently, when the plastic cools, the arms of each flosser tend to shrink inwardly toward each other, thereby reducing tension in the strand of floss. Since the Nylon floss is stretched a greater amount than handle shrinkage, the Nylon floss remains stretched and relatively taut even after the shrinkage of the arms toward each other.

Some flossers use fiber such as multi-filament ultra high molecular weight polyethylene (UHMWP) which stretches very little. When handles for these flossers cool after injection molding and the arms shrink inwardly, the UHMWP floss does not have the large pre-stretch of Nylon floss, and consequently, the floss between the arms becomes slack.

The prior art includes various handles designed to remove slack that develops during use when the floss stretches, including Applicant's prior U.S. Pat. No. 5,692,531 which discloses various configurations of finger or trigger-type projections that extend from the handle and cause divergence of the arms to which the floss is attached.

Also known is a two-component device comprising a handle and a separate flosser head with slack floss, where the flosser head is fully separable from the handle. When the flosser head is attached to the handle a latch element both spreads the arms of the flosser head slightly and removably secures the flosser head to the handle. These flosser heads are replaceable, while the handle is retained and used repeatedly. This flosser solves the slack problem prior to use, but introduces a variety of disadvantages. First, this device requires the user to retain the handle; thus, the user must either carry the handle with him/her or leave it at home and use the flosser only at home. Second, the user has the inconvenience of assembling and disassembling the components. Third, the overall device is relatively large, and the two parts require separate molds and separate manufacturing phases, all being more expensive. Fourth, the floss head can disengage in the mouth and become a swallowing or choking hazard.

SUMMARY OF THE NEW INVENTION

The present invention provides a new one-piece injection-molded dental flosser that stretches the floss when the user prepares the device for use. Prior to such stretching, the new device is generally flat and unusable, with a handle part and a flosser part including floss that is slack, namely, not taut or perfectly linear. Stretching the floss is achieved in the new device by bending the flosser head part relative to the handle, whereby a projection from the handle functions first as a cam to drive the arms of the flosser to be slightly more separated, and second as a latch to lock the flosser head in the bent orientation, which thus maintains the arms more separated and the floss taut.

In a preferred embodiment of this device, the latching is permanent and after use the device is discarded. In another embodiment the latching is secure but is also releasable, allowing return of the flosser head to be generally flat with the handle.

The bent orientation has a further significant advantage, in that a flosser of this overall shape is easier and/or more effective for some persons to use, especially between the back teeth.

Finally, the new flosser achieves the above advantages while being a relatively flat one-piece product which can be fully made in a single injection molding step. As with many other disposable flossers, this one can be manufactured in a multi-cavity mold, where a plurality of cavities are aligned and a long strand of floss is extended through the arm portions of said aligned cavities. This injection molding manufacturing process with the floss molded "in situ" into the arm portion is known in the prior art as may be seen in Applicant's above-noted prior U.S. Patents.

There are numerous ways to latch the flosser head into a bent position relative to the handle. The preferred structure, according to the present invention, is to use a camming projection extending from the center of the distal end of the handle to engage cam follower parts in the flosser head, which are actually a combination of a catch portion to lock the flosser head in the inclined position and adjacent cam follower portions for the projection to drive the arms of the flosser head apart and stretch the floss.

Dental flossers of the present invention include but are not limited to the following structural variations.
1. The flosser head and handle are both generally flat and both lie generally in the same plane, until the flosser head is bent to an inclined position relative to the handle.
2. In a bendable head flosser the latch may permanently or releasably maintain the flosser head bent in the inclined position.
3. The latch comprises one element on the handle and a mating element on the flosser head.
4. The flosser includes a floss tensioning means that is activated when the flosser head is bent.
5. The floss tensioning means is also part of the latch.
6. The floss tensioning means comprises a cam that drives the proximal ends of the flosser head arms apart, thus driving the distal ends of the arms to diverge slightly.
7. The floss tensioning means comprises a cam which both drives the proximal ends of the flosser head arms apart, thus driving the distal ends of the arms to diverge, and includes a latch component which restrains the flosser head in its bent position relative to the handle.
8. The floss tensioning means is on or is part of the flosser head.
9. The flosser head and handle in said first position both lie generally in the same plane.
10. The flosser head comprises a base part and attached thereto the proximal ends of two spaced apart arms, each of said proximal parts having a contact surface adapted to be engaged and urged by said floss tensioning means for urging said arms to diverge from each other.
11. The contact surfaces of the flosser arms comprise shoulders spaced apart and facing each other and between which a cam element is introduced, driving said contact surfaces apart, thus driving said arms' distal ends apart.
12. The flosser head comprises a base part and two arms, each arm having a proximal part extending from said base and a distal part, each proximal part having a contact area adapted to be driven by the floss tensioning means for urging the distal parts of said arms to diverge.
13. The flosser head and handle and hinge part between said head and handle are contiguous parts of a single molded device.
14. The flosser handle, hinge and floss tensioning means comprise contiguous parts of a single injection molded plastic.
15. The flosser handle and flosser head are generally coplanar in said first position, and said combination cam and latch means extends from said handle and out of said plane of said device.

Embodiments of the invention, illustrative of several modes in which applicants have contemplated applying the principles are set forth by way of example in the following description and are shown in the drawings and are particularly and distinctly pointed out and set forth in the appended claims.

Other structures are possible which may separate these two functions of camming and latching, so that there is a latch mechanism and a separate camming mechanism to urge the arms apart. The camming mechanism could be an element extending from the handle or it could be an element associated solely with the flosser head of this device.

DETAILED DESCRIPTION OF THE PREFERRED EMBODIMENTS

Figure 1:
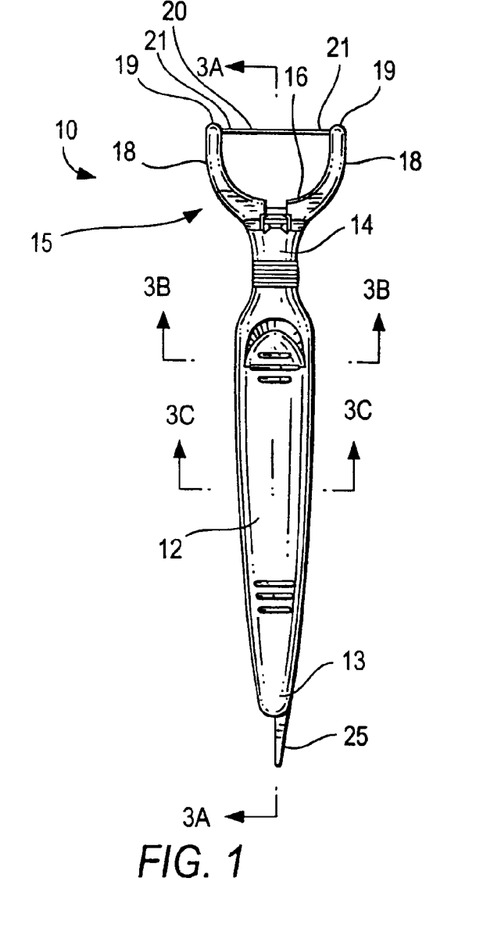
FIG. 1 is a top plan view of the new dental flosser in initial flat form.
Figures 1A, 1B:
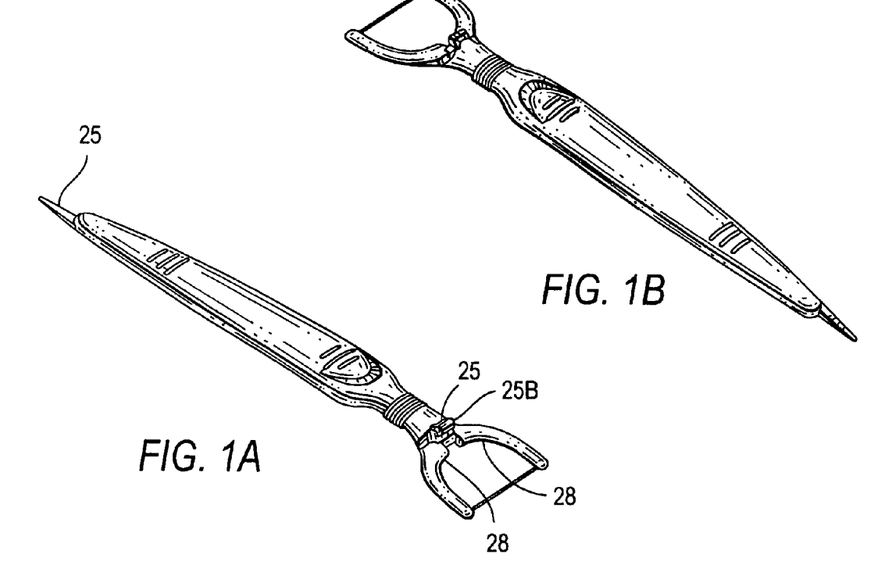
FIG. 1A is a top right side perspective view of the new flosser of FIG. 1.
FIG. 1B is a top left side perspective view of the new flosser of FIG. 1.

First Embodiment:

FIG. 1 one shows the new dental flosser 10 having a handle 12 with proximal end 13 and distal end 14, and a flosser head part 15 having a base 16 and a pair of spaced apart arms 18, each arm having a distal tip end 19. A strand of dental floss 20 extends between the tips of the arms with the ends of the floss 21 secured in the ends 19 of the arms. This floss is initially slightly slack because of the molding process when using UHMW floss.

Figures 2, 3A:
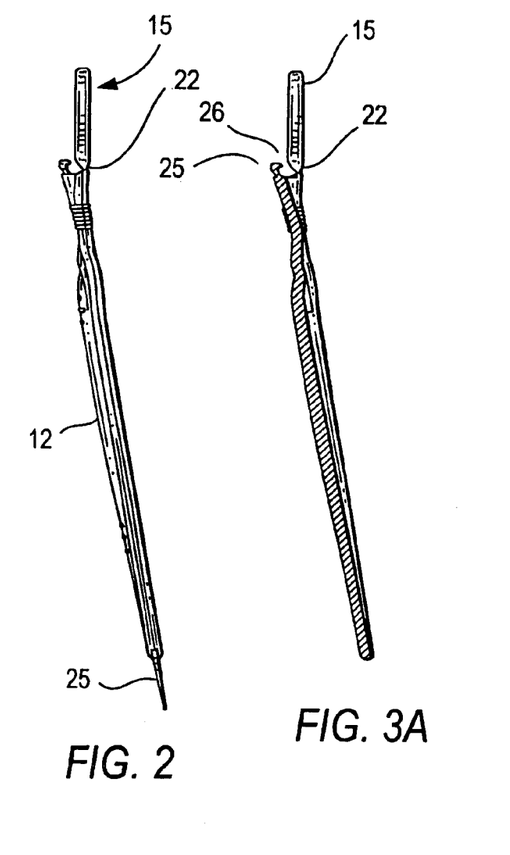
FIG. 2 is a right side elevation view thereof.
Figure 3B:
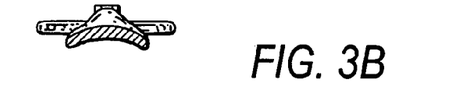
FIG. 3 is a sectional view taken along line A-A in FIG. 1.
Figure 3C:
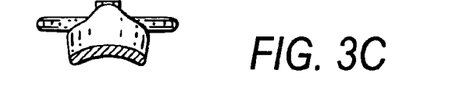
Figure 4:
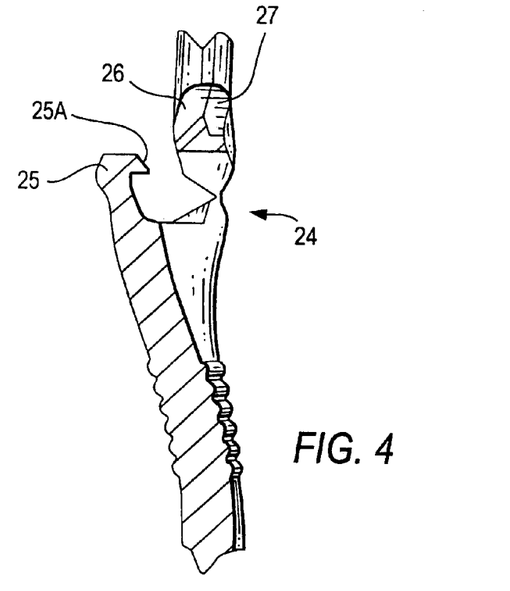
FIG. 4 is a detail of FIG. 3.

FIG. 2 shows that the flosser head portion 15 is connected to the handle 12 by a living hinge 22 which is a thin portion of the injection molded plastic having thickness of approximately 0.012 inches.

Figure 6:
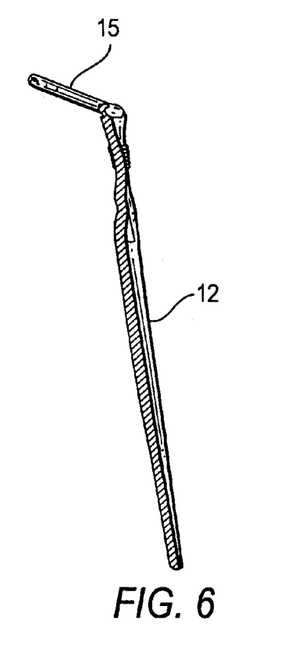
FIG. 6 is a sectional view taken along line 6-6 of FIG. 5.
Figure 7A:
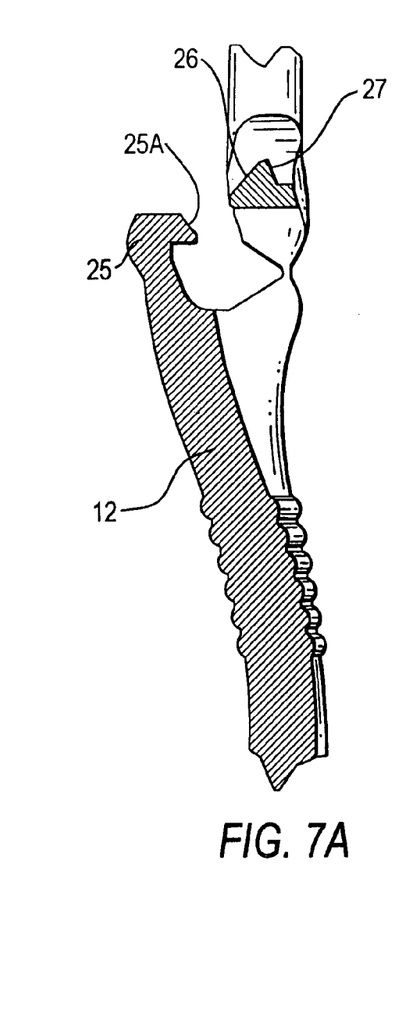
FIGS. 7A, 7B, 7C and 7D are fragmentary sectional views showing stages of bending and latching the flosser head relative to the handle.
Figure 7B:
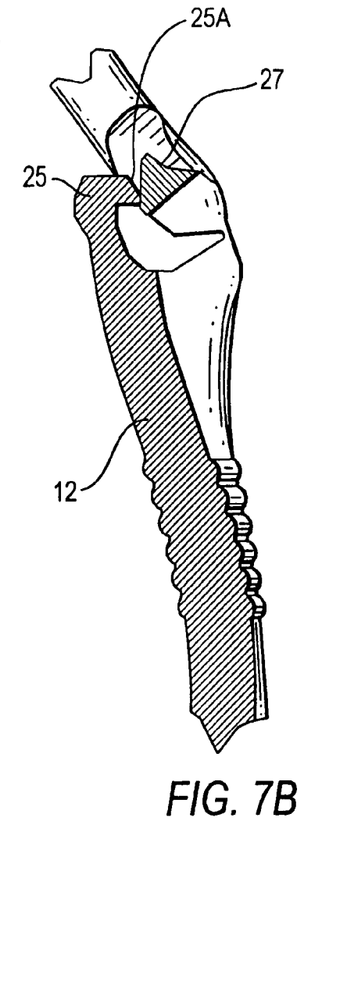
Figure 7C:
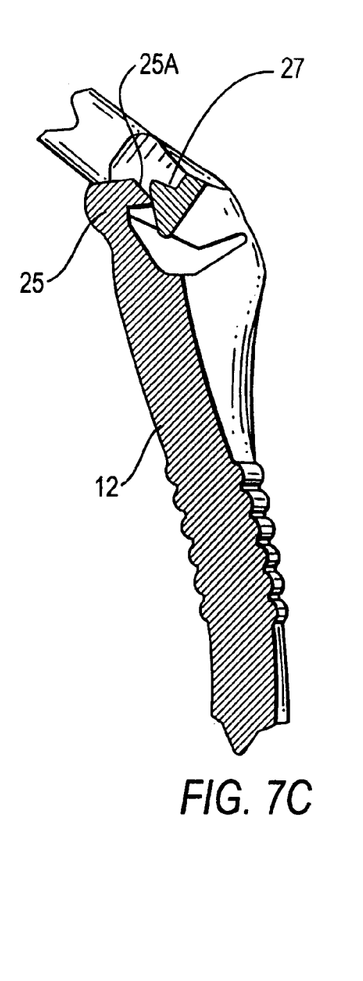
Figure 7D:
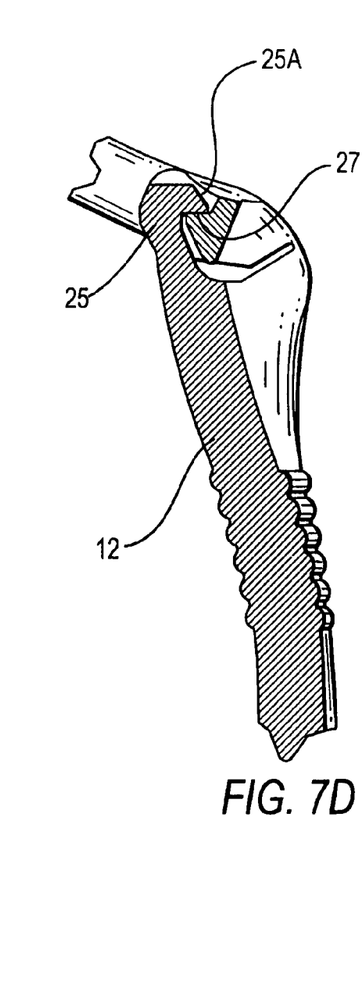

This flosser is typically packaged in the flat state as seen in FIGS. 1, 2, 3, 1A and 1B. For use, the flosser head portion 15 is pivoted relative to the handle 12 to a final assembled position as seen in FIGS. 5 and 6 where the flosser head is moved about 70° from the generally flat plane of its initial state, however this angle may vary. To alter the flosser from its flat state in FIG. 1 to its assembled and bent state in FIGS. 5 and 6, the flosser head is simply bent about the hinge 22 until a projection 25 and its hook 25A engages a catch 26 with its engagement edge 27 on the flosser head, where said hook latches and locks onto the catch portion, and the head is fixed in its angled position.

Figure 8:
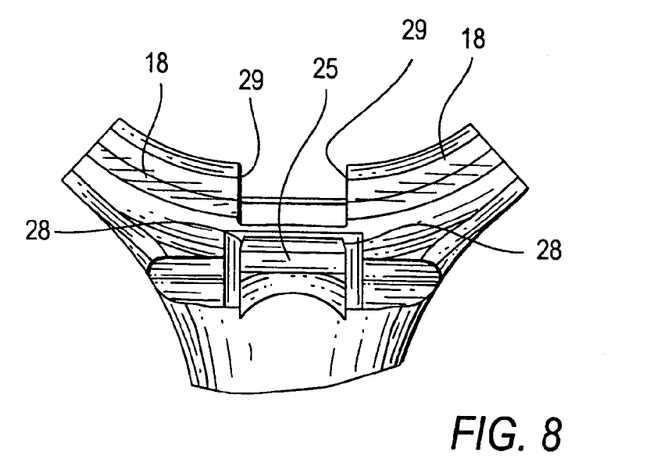
FIG. 8 is an enlarged fragmentary top plan view of the cam and latch element of FIGS. 3 and 4.
Figures 9, 10:
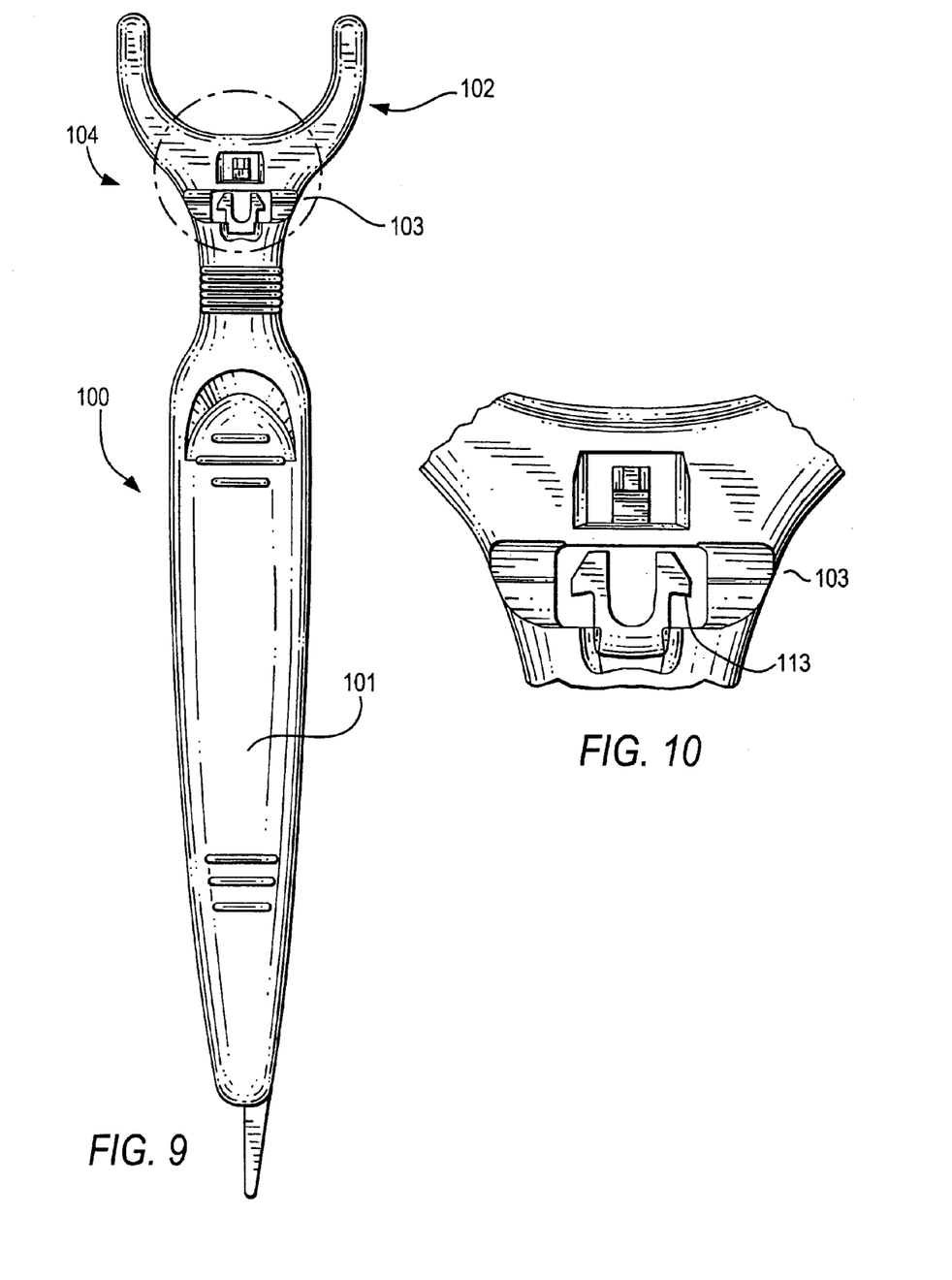
FIG. 9 is a top plan view of the new flosser.
FIG. 10 is a fragmentary detail view of the neck portion of the flosser of FIG. 9.
Figures 11, 12:
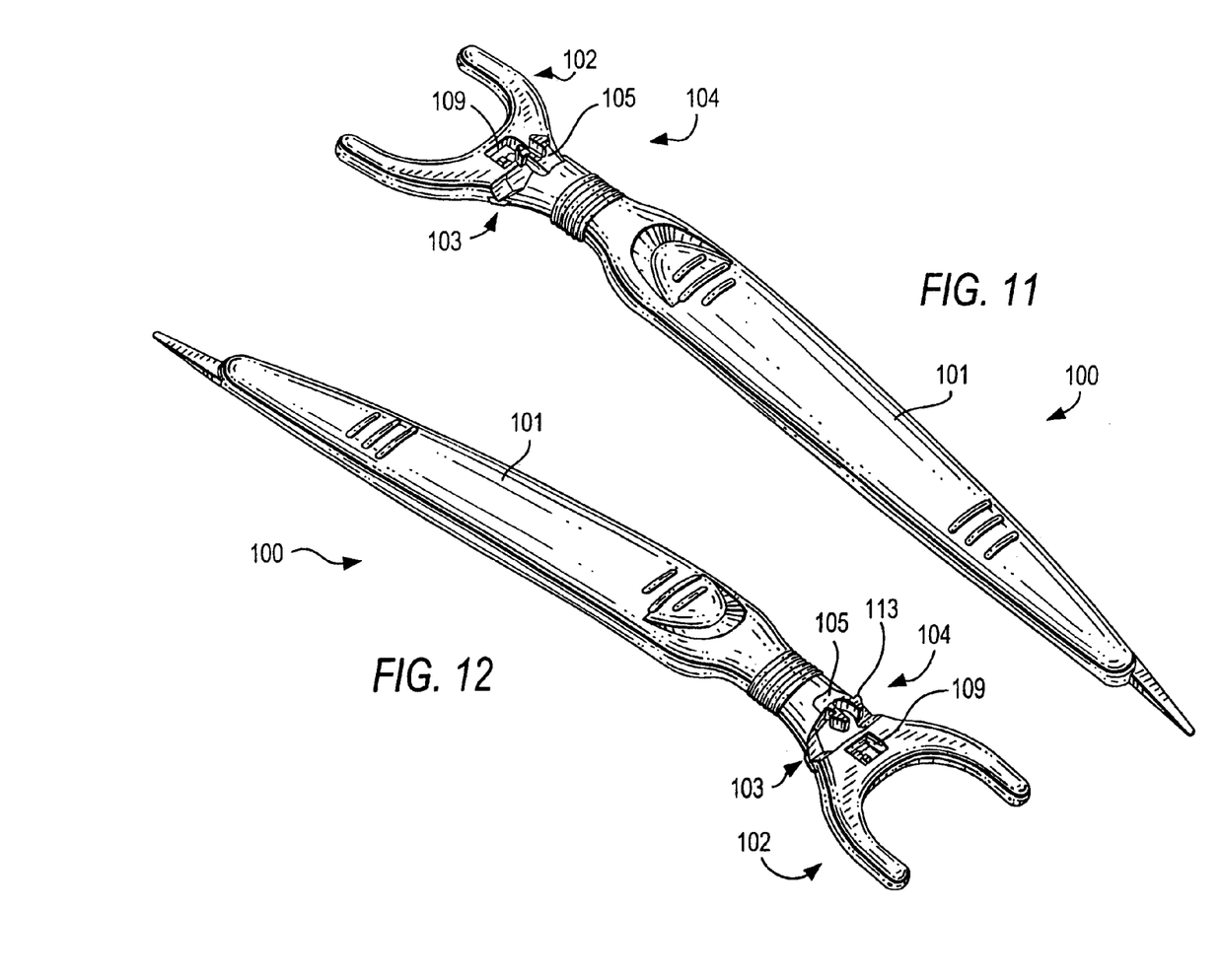
FIG. 11 is a top, left side and rear perspective view.
FIG. 12 is a top, right side and front perspective view.
Figure 13:
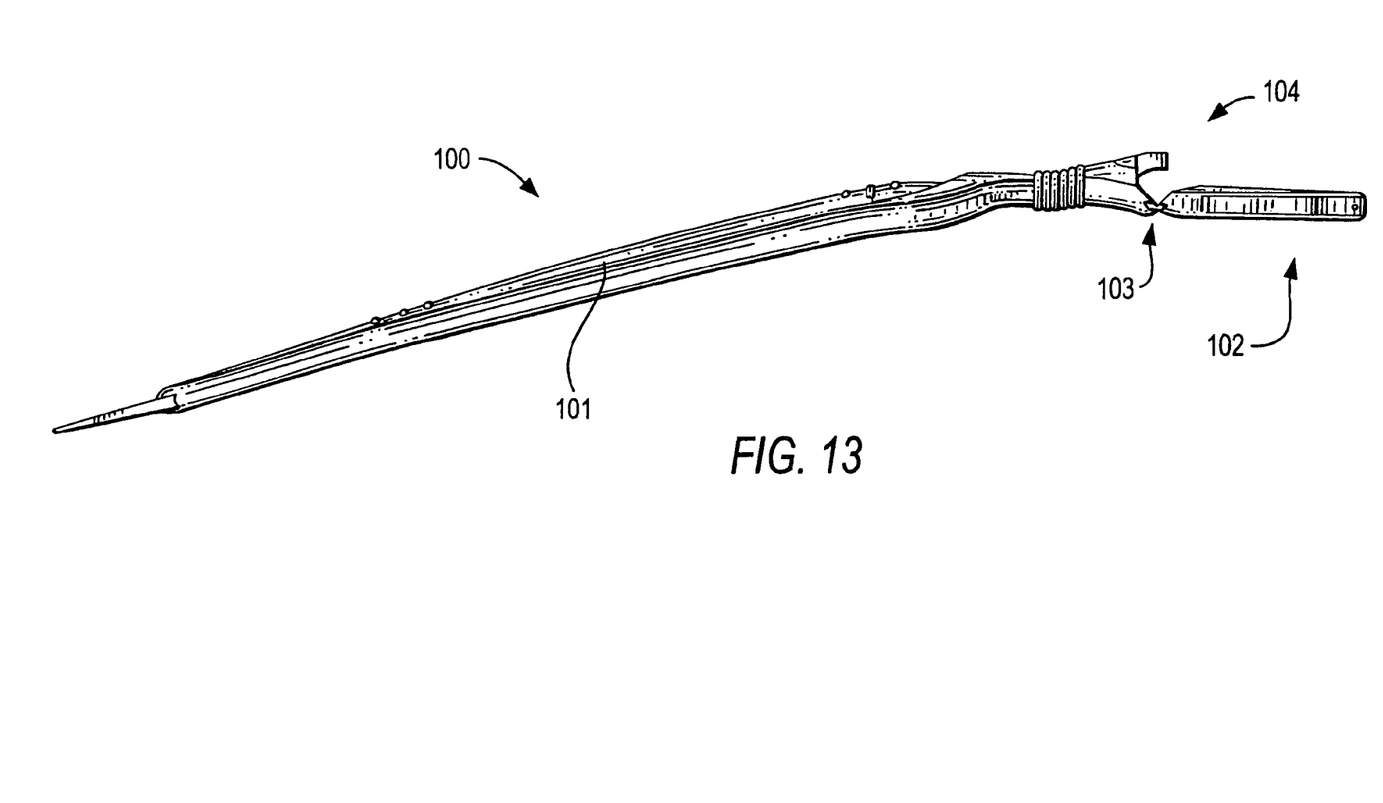
FIG. 13 is a right side elevation view, the left side is the minor image.
Figure 14:
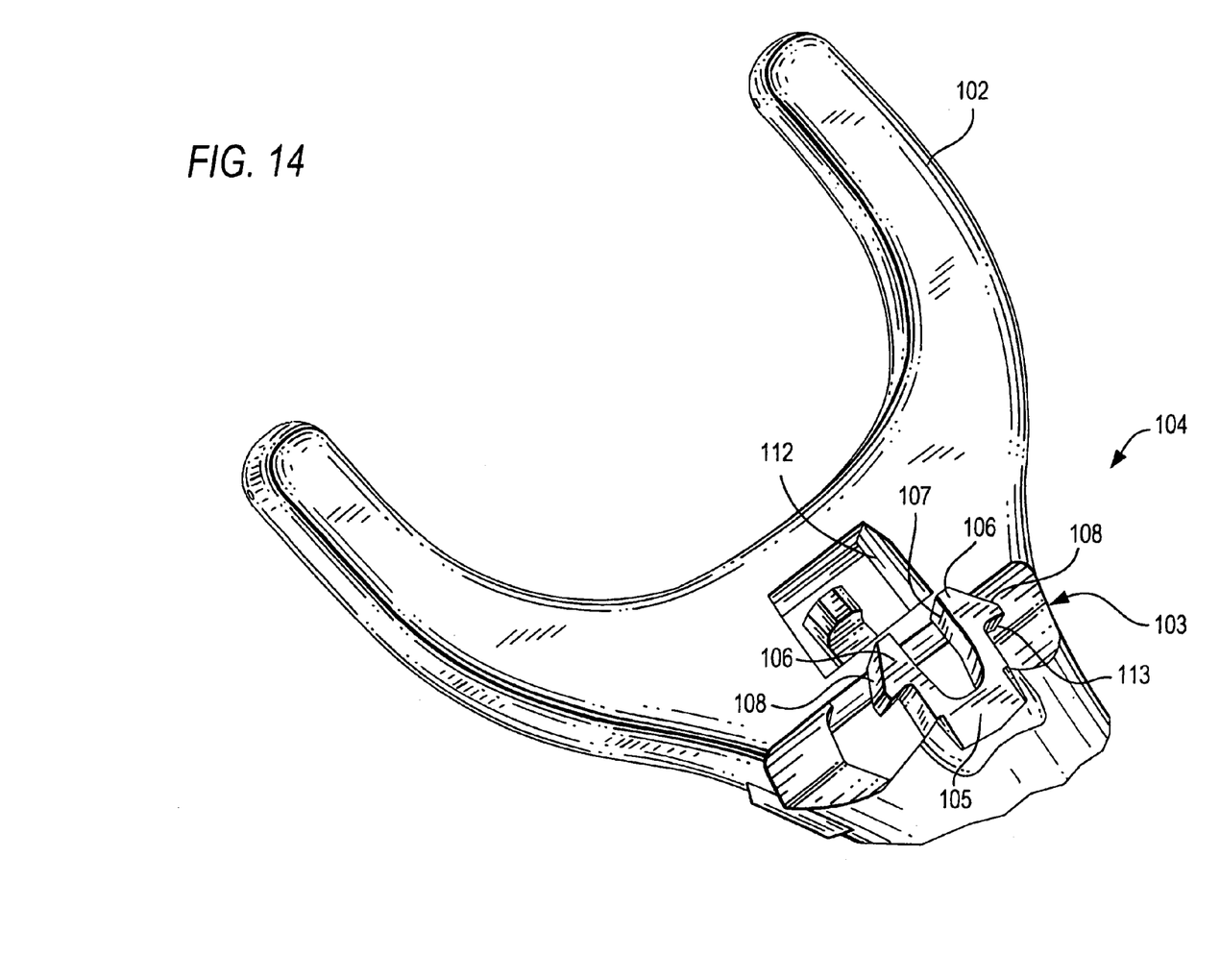
FIG. 14 is a fragmentary detail top perspective view of the head and latch of the flosser of FIGS. 9 and 10.
Figure 15:
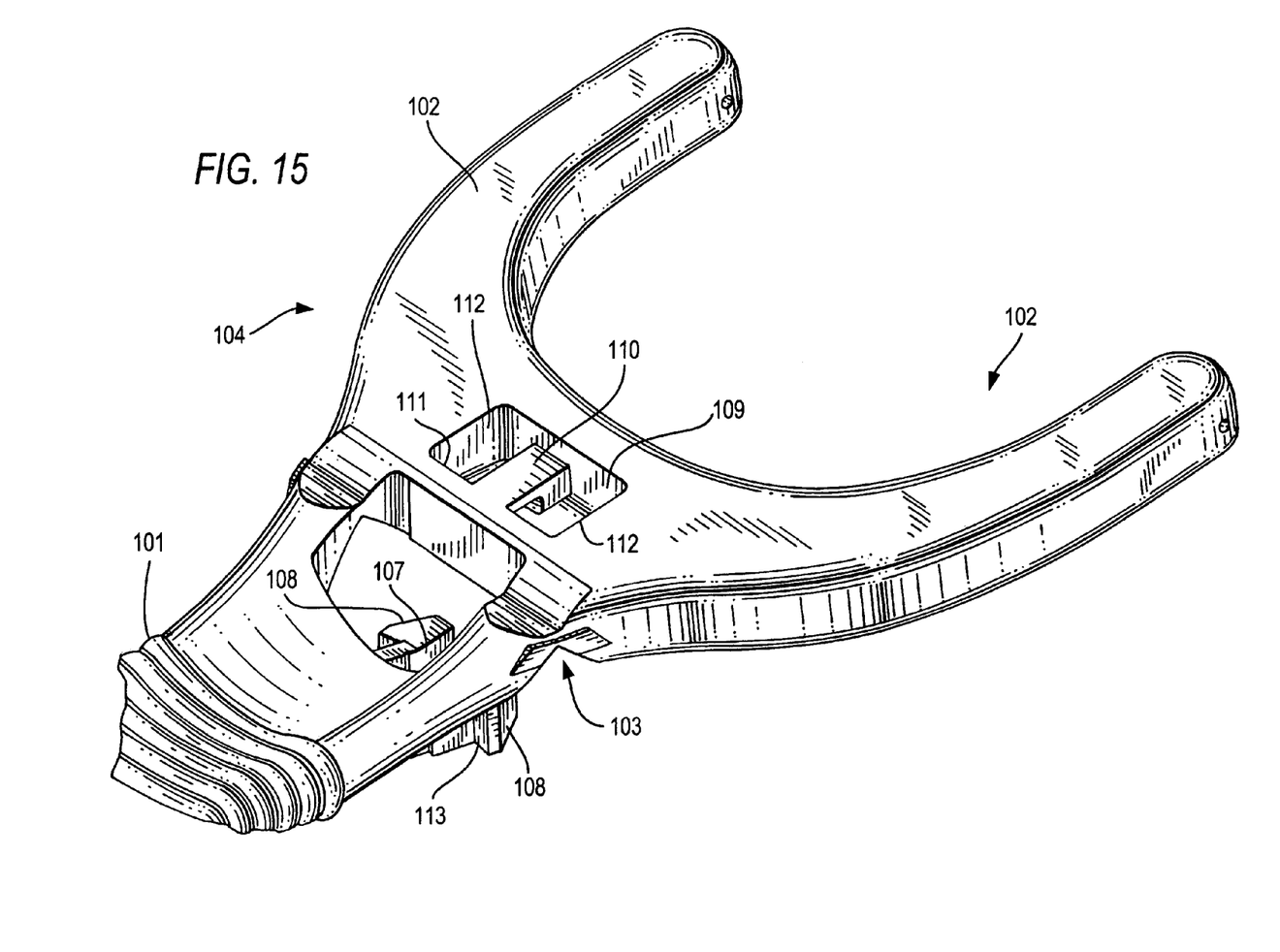
FIG. 15 is a fragmentary detail following perspective view of FIG. 14.

The projection 25 is furthermore a cam where its opposite side surfaces 25B are tapered or chamfered, and as they engage the bottom and proximal ends 29 of arms 18, as seen in FIG. 8, the chamfered surfaces 28 function as cams and drive the arms 18 slightly apart by an amount of approximately 0.002 inches causing the distal ends 19 of the arms 18 to become spaced apart farther than their original amount, thus enhancing the tautness of the floss 20 spanning the distal ends of the arms. This latch serves the dual function of securing the flosser head 15 in an inclined position and simultaneously urging the two arms 18 of the flosser head to be slightly more separated and to stretch the slack floss to be taught.

Thus, this invention provides a dental flosser which has many desirable attributes, namely, (a) being totally disposable, if so desired by the user, (b) being extremely inexpensive in that it is a one-piece product that can be injection molded in multi-cavity molds and is relatively thin, consuming little plastic, (c) being particularly attractive, and (d) including a pick 25 at the proximal end of the handle. It provides the stretching of the floss feature prior to use in a simple, inexpensive and elegant manner by using a portion of the handle itself to engage and maneuver and cam the arms of the flosser head to be farther apart.

FIGS. 7A-7D show the sequence of stages of bending the flosser head 15 to engage the latch and cam projection 25 of the handle 12. As seen, the latch 26 has a tooth or hook part 27 which slides over tapered surface 25A until hook 27 locks under hook 25A. Depending on the tolerances and angles, the flosser head may be permanently locked in this bent position or it may be releasable.

FIG. 8 shows how the projection 25 achieves the camming action to drive the arms 18 farther apart when the flosser head is bent. Tapered surfaces 28 on each side of projection 25 engage the exposed end surfaces 29 of arms 18 when the flosser head is bent to the position shown in FIG. 7B. As the flosser head is further bent per FIGS. 7C and 7D for the latching function, the surfaces 28 push harder against arm end surfaces 29, driving them to slightly diverge. The distal ends of the arms 18, because of their configuration and distance from the contact surfaces 28, have greater divergent movement than the movement apart of surfaces 28. The divergence of the arms' distal ends is sufficient to stretch the floss to eliminate the slack.

With the present invention, the flosser can be generally flat, and can be bent to the desired configuration, which bending simultaneously causes the arms to diverge enough to tighten the floss. Causing the flosser head arms to diverge and tighten the floss may be achieved in many different ways while still employing a one piece flosser device that is bent into a three-dimensional configuration. In certain embodiments, after the flossing head is bent and latched, tension in the floss may help keep the latch secure. For example, where the cam surface is also the latch surface, the reaction forces of the forced-apart arms will cause tighter engagement of the latch. This would occur, for example, if the combination latch and cam element were in contact with the surface of an arm being pushed away. in the embodiment t of FIGS. 7A-7D and 8 the cm surface is separate from the latch surface. It could be designed for the tension to urge tighter latching even with the cam and latch surfaces being different.

Second Embodiment:

As seen in FIGS. 9-13 the new flosser 100 has a handle part 101, a flosser head part 102, a hinge 103, and a latch 104. The head part 102 has two spaced apart arms which are spanned by a strand of dental floss (not shown). This floss is molded 'in situ' per a known injection molding process.

The handle and head are integrally connected by thin hinge portion 103, so that the head can bend from the generally flat condition as seen in FIGS. 9-13 to a bent and latched condition.

The operation of the new flosser is as follows: As seen in FIGS. 14, 15 and 9-12, the latch 104 comprises a bifurcated stem 105 terminating in a pair of spaced apart half arrows or hooks 106, each with inside wall 107 and tapered outside wall 108.

This stem 105 extends integrally from the handle 101. Aligned with this stem is an aperture 109 in flosser head 102 with a lock 110 extending integrally from a proximal wall 111 of the aperture 109. The side walls 112 of the aperture, see FIGS. 12-14, function as catch edges to engage and latch with the lock edges 113 at the rear of the half arrow heads (hooks).

In operation, the head 102 is bent upward about hinge 103, until the latch stem 105 starts to enter aperture 109. The bifurcated arrow heads are too wide for this aperture, and by their angled outer surfaces 108 are cammed toward each other, and thus resiliently bend toward each other until they have a combined breadth sufficiently small to pass through the aperture.

Figure 16:
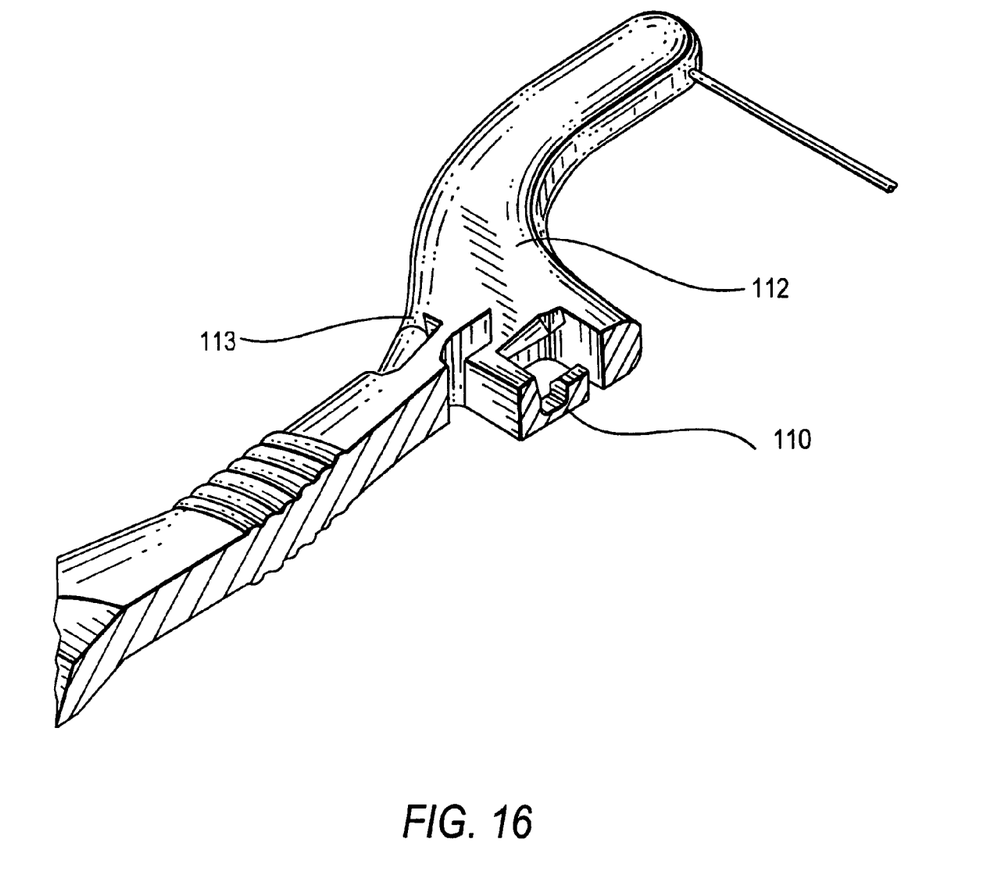
FIG. 16 is a fragmentary top, rear and right side perspective view of the flosser of FIG. 9 as shown as cut by a central vertical axial plane.
Figure 17:
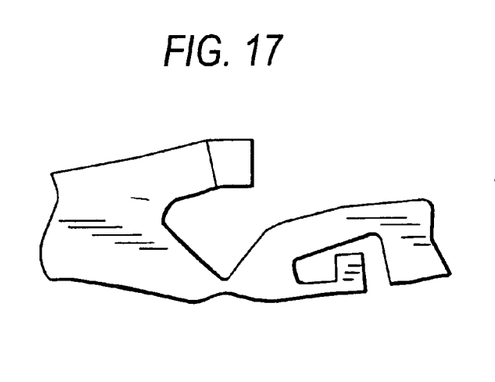
FIGS. 17-22 show a sequence of views of the latch going into engagement.
Figure 18:
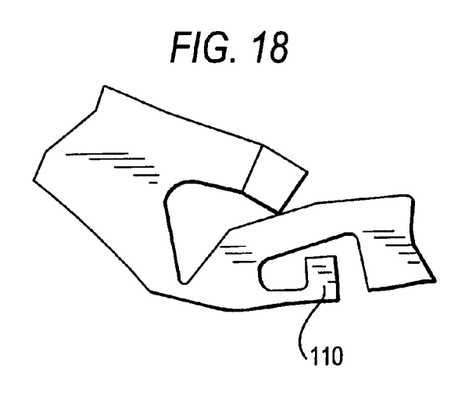
Figure 19:
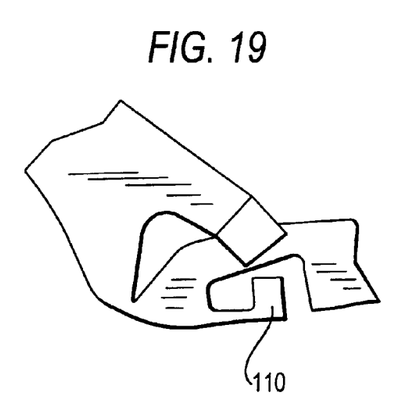
Figure 20:
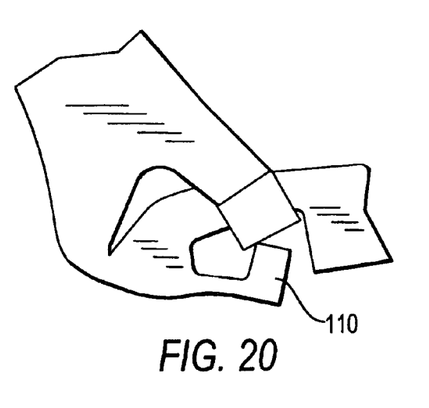
Figure 21:
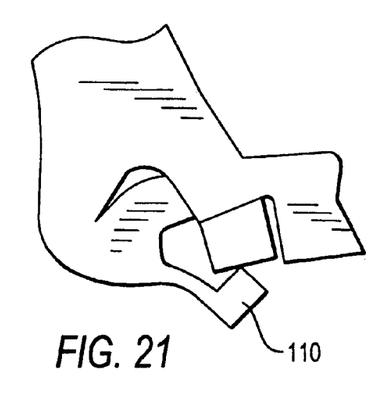
Figure 22:
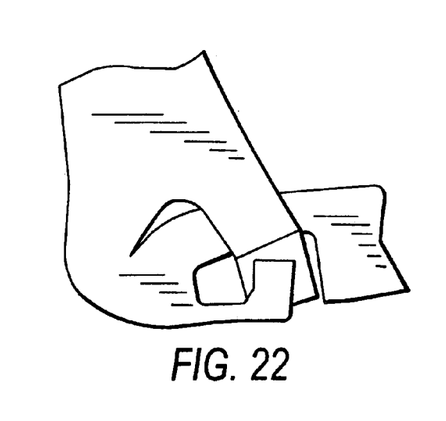

As seen in FIGS. 17-22 which relate to FIG. 16, the flosser shown in a cut-away state, sliced by a central vertical axial plane so that only one arrow head is visible. FIGS. 18-19 show the stem 105 entering aperture 109. FIG. 20 shows the distal end of stem 105 engaging and pushing lock 110 downward, which bends resiliently. FIG. 21 shows that stem 105 has advanced enough for the half arrows to fully enter the aperture, and "pop" laterally outward because they had been resiliently squeezed together to get through the aperture. Now that they are again spaced apart, generally as they began, they no longer push against the lock element 110, which then springs back to its original position which lands it between the two half arrow heads. These two half arrow heads, with the lock now between them, cannot again converge, and therefore they are locked apart, where their barbs remain locked against the catch edges 113 and 111 of the aperture. This effectively prevents the stem from withdrawing from the aperture and thus locks the head in its bent position relative to the handle.

Figures 23, 24:
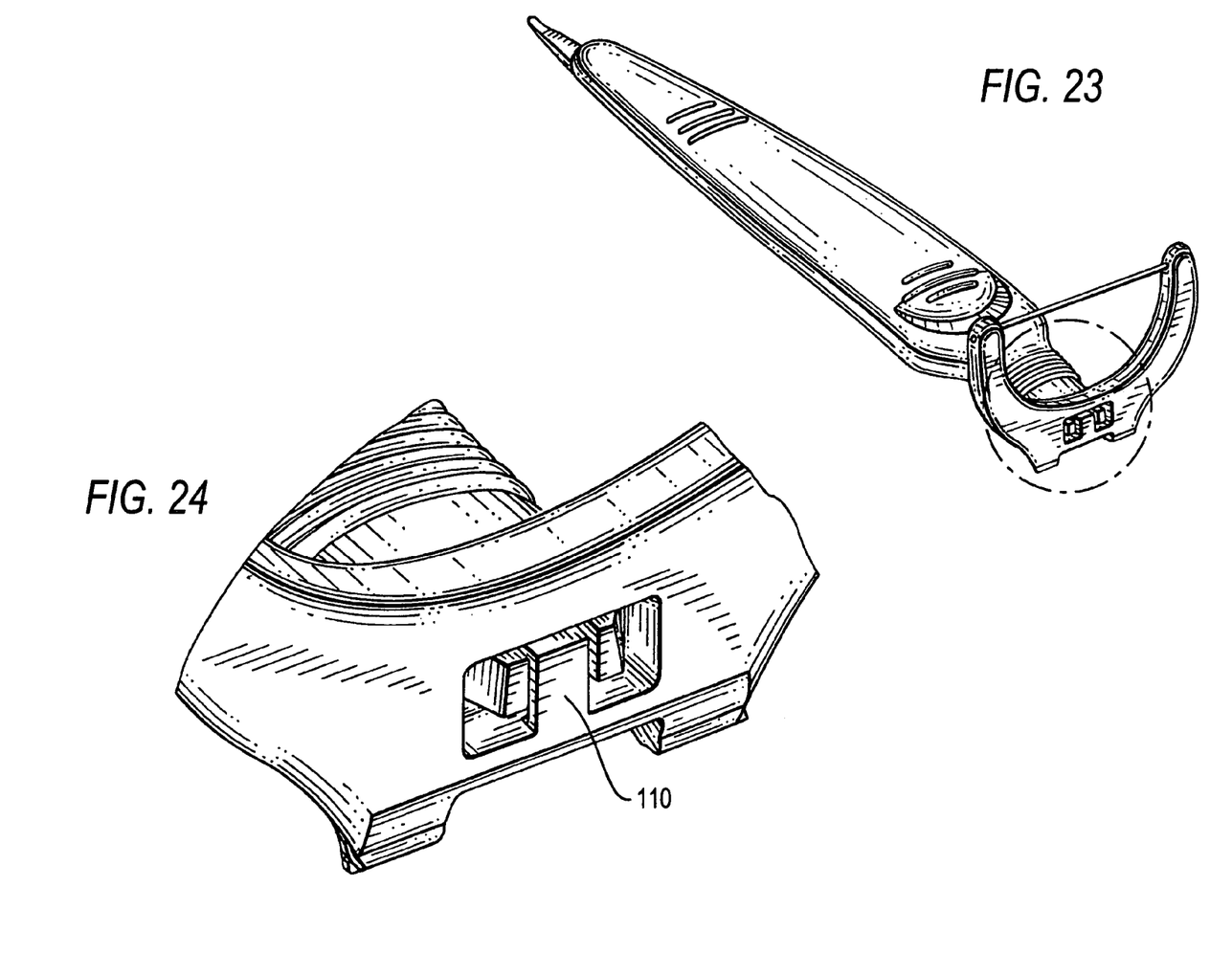
FIG. 23 is a top, rear perspective view of the flosser with the head bent.
FIG. 24 is a fragmentary detail of the latch of FIG. 23.
Figures 25, 26:
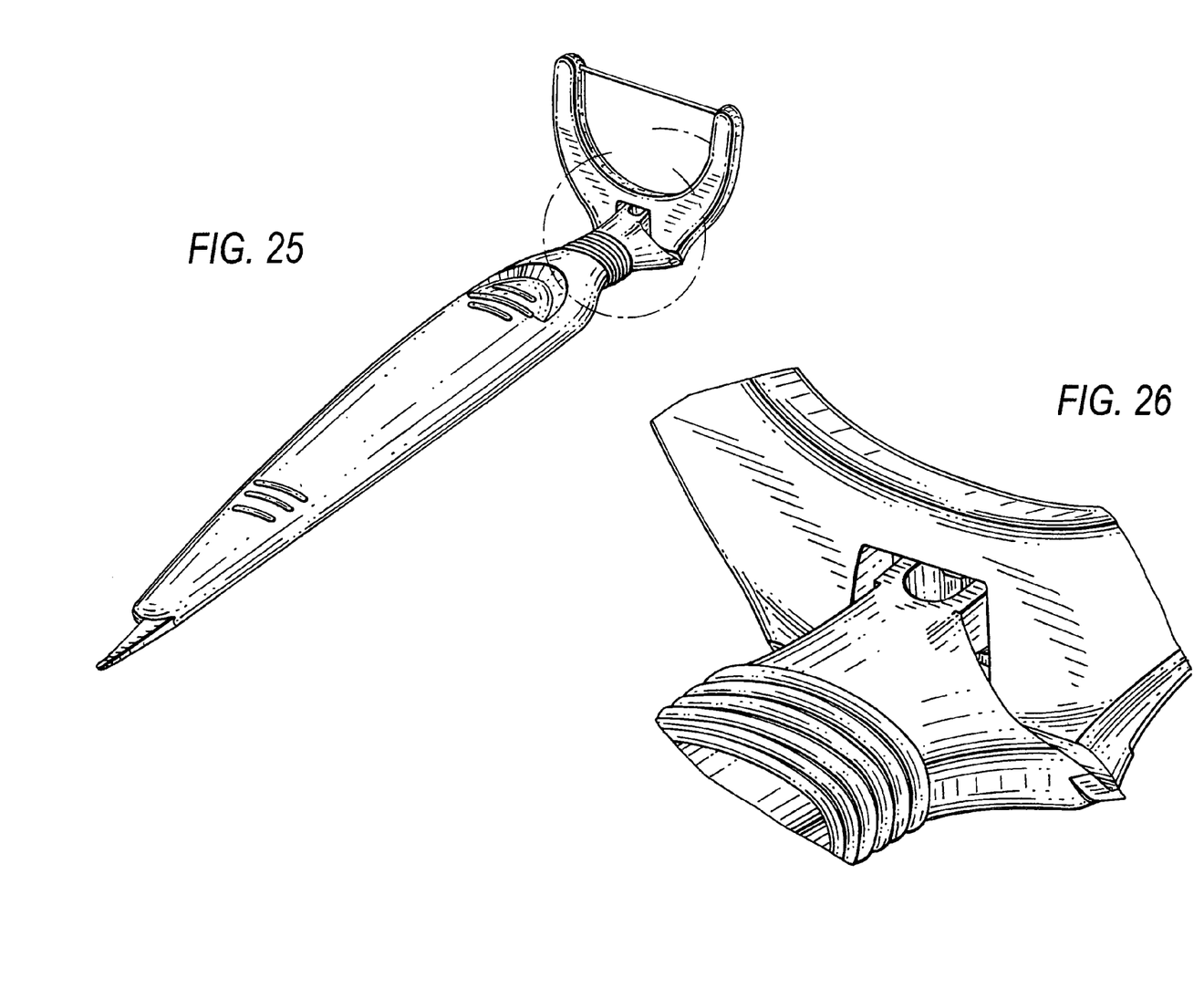
FIG. 25 is a top, rear perspective view of the Flosser of FIG. 23.
FIG. 26 is a fragmentary detail of the latch of FIG. 25.

FIGS. 23-26 provide additional illustrations of the latch. In FIGS. 23 and 24 it is already shown how the head is bent, the bifurcated half arrow heads have advance enough to have re-separated, and the lock element 110 is now between the inside edges of the half arrow heads. FIGS. 25 and 26 demonstrate the same situation as seen from the top and front view of the flosser device.

While there has been shown and described herein several embodiments of the present invention, it should be readily apparent to persons skilled in the art that numerous modifications may be made therein without departing from the true spirit and scope of the invention. Accordingly, it is intended by the appended claims to cover all modifications which come within the spirit and scope of the invention.

The invention claimed is:

1. A dental flossing device comprising:
   a. a handle having proximal and distal ends,
   b. a flosser head extending from said distal end of said handle, said flosser head comprising a base, two spaced apart arms extending from said base and having distal ends, and a strand of dental floss extending between and secured to said distal ends of said arms,
   c. a hinge connecting said distal end of said handle to said flosser head, said flosser head having a first position generally co-planar with said handle, said flosser head being bendable about said hinge to a second position that is angled relative to said handle, said arms in said first position of said flosser head being spaced apart a first distance, and
   d. engagement means securing said flosser head in said second position when it is bent to said second position and urging said distal ends of said arms to be spaced apart a second distance greater than said first distance to thus stretch said strand of dental floss to be more taut.

2. A dental flossing device according to claim 1 wherein said flosser head and said handle comprise a contiguous one-piece molded element.

3. A dental flossing device according to claim 1 comprising plastic selected from the group consisting of ultra high molecular weight polyethylene, polypropylene, polystyrene and Nylon.

4. A dental flossing device according to claim 1 wherein said engagement means is adapted to permanently hold said flosser head in said second position once said flosser head is bent to that position.

5. A dental flossing device according to claim 1, wherein said engagement means is adapted to releasably hold said flosser head in said second position, and to allow said flosser head to return to said first position.

6. A dental flossing device according to claim 1, wherein said engagement means comprises a latch part on one of said handle and flosser head parts and a catch on the other of said parts.

7. A dental flossing device according to claim 1, wherein said engagement means comprises a projection extending from said handle and a catch on said base of said flosser head.

8. A dental flossing device according to claim 7, wherein said projection comprises a stem having a hook on its distal end.

9. A dental flossing device according to claim 8, wherein said projection is situated generally centrally of said handle.

10. A dental flossing device according to claim 7, wherein said base and said arms of said flosser head define a generally U shape, and said arms of said flosser head in said first position have proximal ends spaced apart a distance d, and said projection has a width dimension slightly greater than distance d, said projection, when said flosser head is bent to said second position, being inserted between said proximal ends of said arms and urging said arms to be spaced farther apart than distance d, to thus stretch said strand of floss secured between said distal ends of said arms.

11. A dental flossing device according to claim 1, wherein said arms of said flosser head are spaced apart a first distance in said first position of said flosser head, and are spaced apart a greater distance in said second position of said flosser head, and said engagement means further comprises a cam element which extends from said handle and which engages said flosser head and urges said arms of said flosser head to move to said further apart distance when said flosser head is moved to said second position angled relative to said handle.

12. A dental flossing device according to claim 1, wherein said flosser head further comprises opposite wing elements extending from said base, each of said wing elements being bendable about an axis transverse of the bend axis of said hinge, whereby in said second position of said flosser head, each of said wing elements when bent about its axis engages and latches to said handle to hold said flosser head in said second position.

13. A dental flossing device according to claim 12, wherein said wing elements, when they latch onto said handle also urge said arms apart to enhance tautness of said strand of floss extending between said arms.

14. A dental flossing device according to claim 1, wherein said handle further comprises floss stretching means which extends from said handle and engages and urges apart said arms of said flosser head when said flosser head is moved to said second position.

15. A dental flossing device according to claim 1, wherein said flosser head in its second position is bent to an angle in the range of 10 to 100 degrees to relative to said handle.

16. A dental flossing device according to claim 1, wherein said strand of dental floss comprises ultra high molecular weight polyethylene and said handle and flosser base and arms comprise an injected molded plastic to which said strand of dental floss does not chemically bond when said device is injection molded.

17. A dental flossing device according to claim 1, wherein said strand of dental floss is generally straight before said flosser head is molded, and said arms of said flosser head shrink slightly toward each other when said flosser head and handle are cooled after being injection molded, such that said strand of dental floss becomes slightly slack.

18. An injection molded dental flossing device comprising as a single molded product:
   a. a handle having proximal and distal ends,
   b. a flosser head comprising a base, a pair of arms spaced apart from each other, each arm having a proximal part extending from said base and distal end, and a strand of dental floss extending between and secured to said distal ends of said arms,
   c. a hinge connecting said distal end of said handle to said flosser head, said flosser head having a first position generally co-planar with said handle, said flosser head being bendable about said hinge to a second position that is angled relative to said handle, and
   d. latch means which irreversibly secures said flosser head in said second position after said flosser head is bent to said second position and secures said flosser head in said second position and urges said distal ends of said arms to diverge.

19. A method of enhancing the tautness prior to use in a dental flosser device formed as a handle and flosser head having two spaced apart arms between which a strand of dental floss extends and is secured, comprising:
   a. bending said flosser head relative to said handle,
   b. while bending said flosser head urging said arms farther apart thus stretching said floss extending there between,
   c. providing latch means to secure said flosser head in said bent position with said arms urged apart and said strand of dental floss thus stretched.

* * * * *